Nov. 25, 1952 F. MEILLAND Plant Pat. 1,148
ROSE PLANT
Filed Sept. 17, 1951
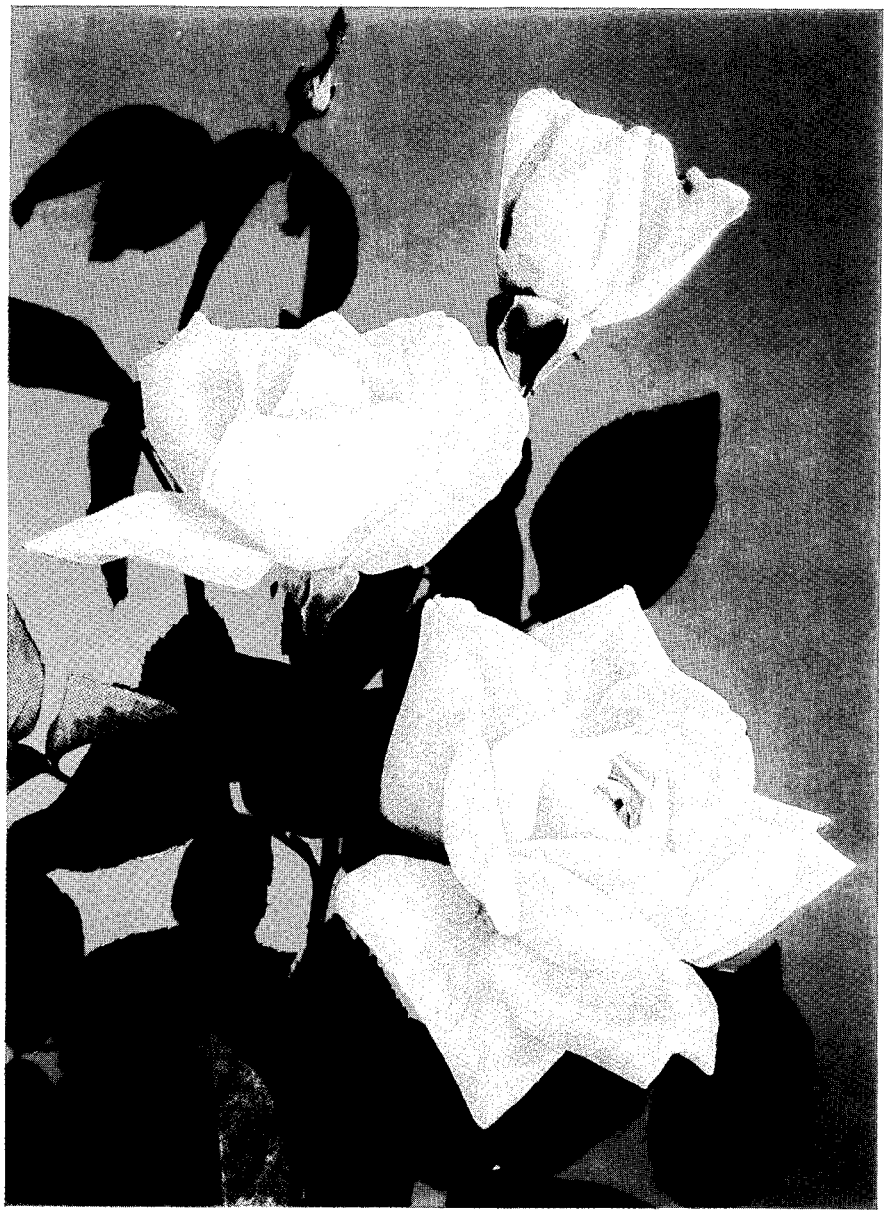
Inventor.
Francis Meilland
By: Robb & Robb
Attorneys.

Patented Nov. 25, 1952

Plant Pat. 1,148

UNITED STATES PATENT OFFICE 1,148

ROSE PLANT

Francis Meilland, Cap Azura, Cap d'Antibes, Alps Maritime, France, assignor to The Conard-Pyle Company, West Grove, Pa., a corporation of Pennsylvania Application September 17, 1951, Serial No. 246,931
In France October 16, 1950

1 Claim. (Cl. 47—61)

The present invention relates to a new and distinct variety of rose plant of the hybrid tea class, originated by me by crossing the variety "Peace" (Plant Patent No. 591) × an unnamed and unpatented seedling which originated as a cross of "Julien Potin" (unpatented) × "Sensation" (unpatented).

As the result of this breeding, I have produced a new variety that is distinctly different from its parents, as well as from any other known variety of this class, although it generally resembles the parent "Peace" in respect to the coloring of its buds and blooms, but usually has a larger area of pink on each outer petal.

While the buds and blooms of "Peace" always present the characteristics of massiveness and magnificence, those of my new variety are distinctly characterized by lightness, delicateness and gracefulness, due basically to the fact that the new variety has fewer flower petals (averaging 25 to 30 petals per flower, in contrast with 50 to 55 for "Peace"), accompanied by a correspondingly proportioned, general scaling down of the size, substance and appearance from the characteristics of "Peace."

Asexual reproduction of the new variety by budding at Tassin-les-Lyon, France, and at West Grove, Pennsylvania, U. S. A., shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.
Class: Hybrid tea.
Parentage: Seedling.
*Seed parent.*—"Peace."
*Pollen parent.*—An unnamed seedling originating as a cross of "Julien Potin" × "Sensation."
Propagation: Holds its distinguishing characteristics through succeeding propagations by budding.

*Flower*

Locality where grown and observed: West Grove, Pennsylvania, U. S. A.

Flowers borne: Singly to stem; on strong, medium length stems.
Quantity of bloom: Free to abundant outdoors.
Continuity: Continuous.
Fragrance: Moderate; tea.
Bud:
*Peduncle.*—Medium length; medium thickness; erect; almost smooth; few greenish hairs and reddish prickles. Color—Cosse Green, Plate V, shaded with Orange-Citrine, Plate IV.
*Before calyx breaks.*—Size—medium. Form—medium length; pointed; ovoid; with foliaceous appendages on the surface of the bud; with slender, cut foliaceous parts extending beyond the tip of the bud equal to ¼ to ½ of its length.
*As calyx breaks.*—Color—Light Viridine Yellow, Plate V, tinged Old Rose, Plate XIII.
*As first petal opens.*—Size—medium. Form—medium length; ovoid. Color: outside—Wax Yellow, Plate XVI, at base, shading to Salmon Color, Plate XIV, at outer edges; inside—shading from Lemon Chrome, Plate IV, at base to Strawberry Pink, Plate I.
*Opening.*—Opens up well.
Bloom:
*Size, when fully open.*—Medium size; 4 inches to 4½ inches.
*Petalage.*—Double; from 25 to 30 petals; arranged regularly; stamens not hidden.
*Form.*—Very high-centered at first; becoming high-centered; petals being at first loosely rolled outward; becoming later, at maturity, loosely rolled outward.
Petals: Medium thickness; with inside and outside satiny.
*Shape.*—Outer—obovate; with apex flat or with one notch. Intermediate—obovate; with apex flat or with one notch. Inner—obovate; with apex flat or with one notch.

This description of a newly opened flower was made from a rose grown outdoors in the month of July, at West Grove, Pennsylvania:

*Color.*—Outer petal: outside surface—Amber Yellow, Plate XVI, at base, bordered with Buff Yellow, Plate IV; inside surface—Lemon Chrome, Plate IV, at base, shading to Barium-Yellow, Plate XVI, with Thulite Pink, Plate XXVI, border. Intermediate petal; outside surface—Pinard Yellow, Plate IV, at base, shading to Baryta- Yellow, Plate IV, on outer surface; inside surface—Lemon Chrome, Plate IV, at base, shading to Naphthalene Yellow, Plate XVI, with Strawberry Pink, Plate I, border. Inner petal: outside surface—Amber Yellow, Plate XVI; inside surface—Lemon Chrome, Plate IV, at base, shading to Empire Yellow, Plate IV, with Light Coral Red, Plate XIII, edging.

This description was made from a rose that was open for three days outdoors in the month of July, at West Grove, Pennsylvania:

*Color.*—Outer petal: outside surface—Naphthalene Yellow, Plate XVI, at base, shading to Cartridge Buff, Plate XXX; inside surface—Barium Yellow, Plate XVI, at base, with Hermosa Pink, Plate I, border. Inner petal: outside surface—Baryta Yellow, Plate IV, shading to Maize Yellow, Plate IV; inside surface—Pinard Yellow, Plate IV, at base, shading to Naples Yellow, Plate XVI, with a little Geranium Pink, Plate I, edging.

*General color effect.*—Newly opened flower—Apricot Yellow, Plate IV, with Thulite Pink, Plate XXVI, border. Three days open—Apricot Yellow, Plate IV, with Hermosa Pink, Plate I, border.

*Behavior.*—Drop off cleanly.

*Flower longevity.*—Cut roses grown outdoors kept at living-room temperature—3 to 4 days in July.

*Reproductive organs*

Stamens: Medium to many; arranged regularly about pistils.

Filaments: Most with anthers; medium length. Color—Light Coral Red, Plate XIII, on outside ones, and inner ones Madder Brown, Plate XII.

Anthers: All open at various times; medium size; occasionally an anther fused with petaloid or pistil.

Pollen: Moderately abundant. Color—Orange, Plate III.

Pistils: Medium number.

Styles: Uneven; medium length; medium-thickness; bunched.

Stigma: Color—Cadmium Yellow, Plate III.

Ovaries: All enclosed in calyx.

Sepals: Permanent; medium length; spear-shaped; recurved.

*Plant*

Foliage:

*Leaves.*—Compound of 3 to 5 leaflets; normal abundance; medium size; leathery; glossy.

*Leaflets.*—Shape—oval with apex acute. Base—round. Margin—simply serrate.

*Color.*—Mature: upper surface—Dark Cress Green, Plate XXXI; under surface—Asphodel Green, Plate XLI. Young: upper surface—Cerro Green, Plate V, bordered with Mineral-Red, Plate XXVII; under surface—Deep Grape Green, Plate XLI.

*Rachis.*—Medium size. Upper side—grooved; prickly. Under side—moderately smooth and occasionally thorny.

*Stipules.*—Moderately long; moderately narrow; with medium length points, turning out at an angle of less than 90°; recurved toward the stem.

*Disease.*—Resistant to mildew and blackspot, as determined by comparison with other varieties of the same class grown under comparable conditions at West Groove, Pennsylvania.

Growth:

*Habit.*—Upright; branched.

*Growth.*—Vigorous.

*Canes.*—Medium heavy.

*Main stems.*—Color—bronze with some grey-green showing. Thorns—many; medium length; pointed downward; with medium length oval base. Prickles—none observed. Hairs—none.

*Branches.*—Color—bronze with some grey-green showing. Thorns—many; medium length; pointed downward; with medium length oval base. Prickles—few; reddish. Hairs—none.

*New shoots.*—Color—grey-green with some bronze coloring. Thorns—many; medium length; pointed downward; with medium length oval base. Prickles—few; reddish. Hairs—none.

I claim:

A new and distinct variety of rose plant of the hybrid tea class, substantially as herein shown and described, characterized as to novelty by its general similarity to the variety "Peace" (Plant Patent No. 591) in respect to the coloring of its buds and blooms, while dominantly differing therefrom by its fewer petals per flower, by a general scaling down of the size, substance and appearance thereof in contrast with "Peace," and usually by a relatively larger area of pink color on each outer petal.

FRANCIS MEILLAND.

No references cited.